US005297540A

United States Patent [19]

Kaiser et al.

[11] Patent Number: 5,297,540

[45] Date of Patent: Mar. 29, 1994

[54] CONTINUOUS PASSIVE MOTION ORTHOSIS DEVICE FOR A TOE

[75] Inventors: Robert T. Kaiser, Mount Laurel, N.J.; George Telepko, Fort Washington, Pa.; Vero Ricci, Collingswood; Berdj C. Kalustyan, Morrestown, both of N.J.

[73] Assignee: Jace Systems, Inc., Moorestown, N.J.

[21] Appl. No.: 827,787

[22] Filed: Jan. 29, 1992

[51] Int. Cl.$^5$ .............................................. A61F 5/00

[52] U.S. Cl. .......................................... 69/27; 482/79

[58] Field of Search ............. 602/30; 128/25 R, 25 B, 128/26; 482/79, 80

[56] References Cited

U.S. PATENT DOCUMENTS

| | | | |
|---|---|---|---|
| 2,250,493 | 7/1941 | Milne | 128/25 B |
| 2,255,066 | 9/1941 | Lamb | 128/25 B |
| 2,397,428 | 3/1946 | Moshier | 128/25 B |
| 4,276,887 | 7/1981 | Hofstein | 128/25 B X |
| 4,665,899 | 5/1987 | Farris et al. | 128/25 B X |
| 4,671,257 | 6/1987 | Kaiser et al. | 128/25 R |
| 4,716,889 | 1/1988 | Saringer . | |
| 4,862,875 | 9/1989 | Heaton | 128/25 B |
| 4,869,499 | 9/1989 | Schiraldo . | |
| 5,010,878 | 4/1991 | Kline et al. . | |
| 5,039,093 | 8/1991 | Collier | 128/25 B X |
| 5,046,487 | 9/1991 | Scott | 128/25 B |
| 5,094,226 | 3/1992 | Medcalf et al. | 128/25 B |

*Primary Examiner*—Richard J. Apley
*Assistant Examiner*—Linda C. M. Dvorak
*Attorney, Agent, or Firm*—Panitch Schwarze Jacobs & Nadel

[57] ABSTRACT

A continuous passive motion orthosis device for a toe of a foot including a base having first and second mounting members for receiving the calf and foot, respectively. A pivotable carriage member is positioned proximate the second mounting member and has a first end for receiving the toe and a second end. A drive mechanism is interconnected between the second end of the carriage member and the base for oscillating the first end of the carriage member about its second end with respect to the second mounting member to thereby move the toe between dorsiflexion and plantar flexion.

10 Claims, 8 Drawing Sheets

CONTINUOUS PASSIVE MOTION ORTHOSIS DEVICE FOR A TOE

FIELD OF THE INVENTION

The present invention relates to exercise devices and, more particularly, to a device which receives a toe of a human patient and passively and continuously exercises the same.

BACKGROUND OF THE INVENTION

In the past, postoperative and posttrauma treatment of patient's joints commonly include immobilization. The affected joints were fixed by casts or traction for an extended duration. As a result of such immobilization, various medical problems commonly arose. In particularly, capsular, ligamentous and articular adhesions, thromboembolism, venos stasis, posttraumatic osteopenia, peripheral edema, muscle atrophy, and the like were commonly attributed to the immobilization.

It is now known that immobilization related medical problems could be reduced or eliminated by early mobilization of the affected joint. It has been found to be advantageous to initiate joint mobilization immediately following orthopedic surgery, in many instances, in the operating and recovery rooms while the patient is still under anesthesia. Specifically, continuous passive motion of the affected joints has been found to be effective in reducing or eliminating the above-referenced medical problems, promoting faster healing, reducing the amount of pain and medications, improving the range of movement of the affected joint after recovery, and the like.

Continuous passive motion devices (CPMs) are typically motor driven and are designed to exercise a particular joint by repeatedly extending and flexing the joint. CPMs are capable of applying continuous motion to the joint in a repeatable, consistent manner and can be adjusted to operate at different speeds and within a defined range of motion. Although CPMs are known, there has not been a CPM which can readily receive and exercise the toe of a human foot. Since CPMs have not been developed which can properly exercise the toe, the injured toe is either immobilized or secured to an adjacent toe by tape or the like.

The present invention is directed to a CPM for a toe of a foot which is equally usable with both the right and left foot of a human patient. Moreover, the CPM of the present invention is versatile in that it allows the patient to assume one of many positions while the toe is being exercised. Consequently, use of the present invention results in comfort to the patient and enhanced rehabilitation of the toe joint.

SUMMARY OF THE INVENTION

Briefly stated, the present invention comprises a continuous passive motion orthosis device for a toe of a foot. A mounting means is provided for securely receiving the foot. A pivotable carriage member is positioned proximate the mounting means and has a first end for receiving the toe and a second end. A drive means is interconnected between the second end of the carriage member and the mounting means for oscillating the first end of the carriage member about the second end thereof with respect to the mounting means to thereby move the toe between dorsiflexion and plantar flexion.

BRIEF DESCRIPTION OF THE DRAWINGS

The foregoing summary, as well as the following detailed description of the preferred embodiment, will be better understood when read in conjunction with the appended drawings. For the purpose of illustrating the invention, there is shown in the drawings an embodiment which is presently preferred, it is understood, however, that the invention is not limited to the specific methods and instrumentalities disclosed. In the drawings.

DESCRIPTION OF PREFERRED EMBODIMENT

Figure 1:
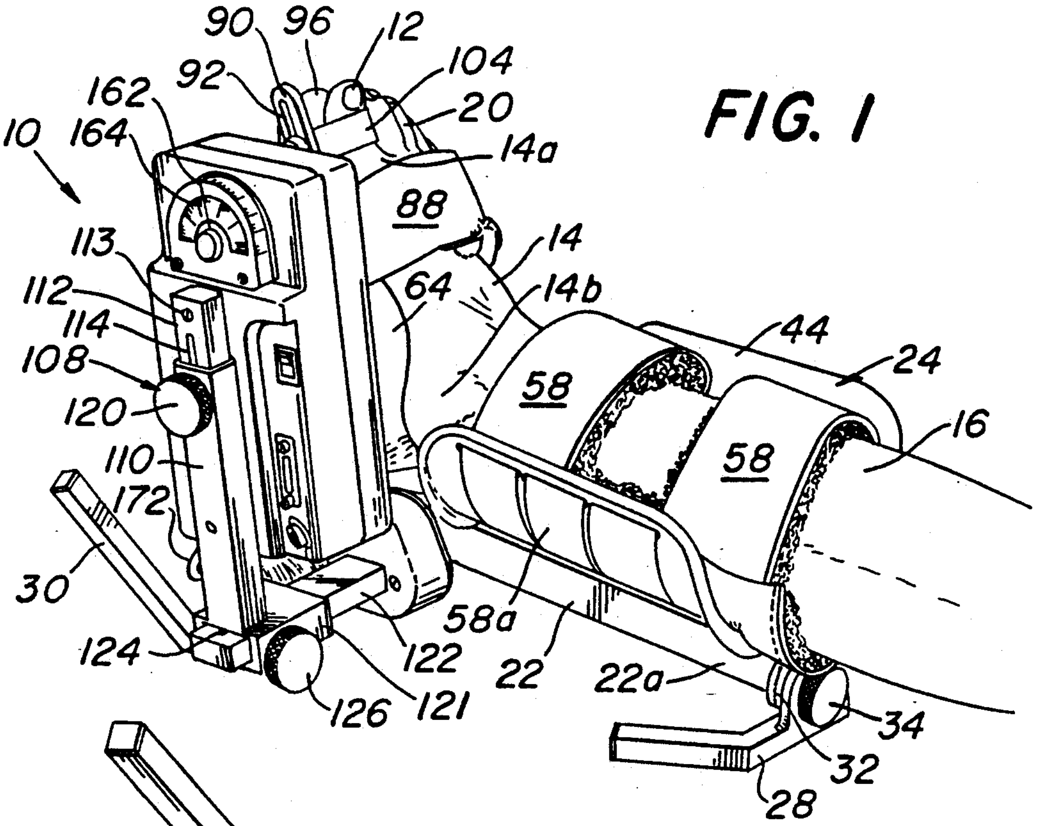
FIG. 1 is a perspective view of a continuous passive motion orthosis device for a toe in accordance with the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the CPM and designated parts thereof. The terminology includes the words above specifically mentioned, derivatives thereof and words of similar import.

Referring now to the drawings in detail, wherein like numerals indicate like elements throughout, there is shown in FIGS. 1 through 9 a preferred embodiment of a continuous passive motion orthosis device (CPM), generally designated 10, for a toe 12 of a foot 14. The foot 14 has a first end 14a connected to the toe 12 and a second end 14b connected to a calf 16. The first end 14a of the foot 14 is pivotably connected to the toe 12 to form a first joint such that the toe 12 is pivotable with respect to the foot 14 about a first joint pivot axis 18 (see FIGS. 4 and 6).

In the present embodiment, it is preferred that the toe 12 be the fifth toe or hallux on the foot 14. However, it is understood by those skilled in the art that the present invention is equally applicable to the second, third, fourth and minimus toes 20 of the foot 14. As is well known, each toe extends from the metatarsal bone (not shown) and is formed by the proximal phalanx, middle phalanx and distal phalanx (not shown) each of which is is respectively pivotally connected to form a joint therebetween. In the present embodiment, it is preferred that the first joint be the joint formed between the metatarsal and proximal phalanx of the toe 12. However, it is understood by those skilled in the art that the other joints of the toe 12 could be aligned on the CPM 10, without departing from the spirit and scope of the invention.

Unless otherwise indicated herein, it is understood that all of the elements of the CPM 10 are preferably constructed of a high-strength, lightweight material, such as aluminum. However, it is understood by those skilled in the art that the present invention is not limited to constructing the CPM 10 of any particular material and that the CPM 10 could be constructed of other high-strength, lightweight materials, such as a composite fibrous and resin material or any suitable polymeric material.

Figure 2:
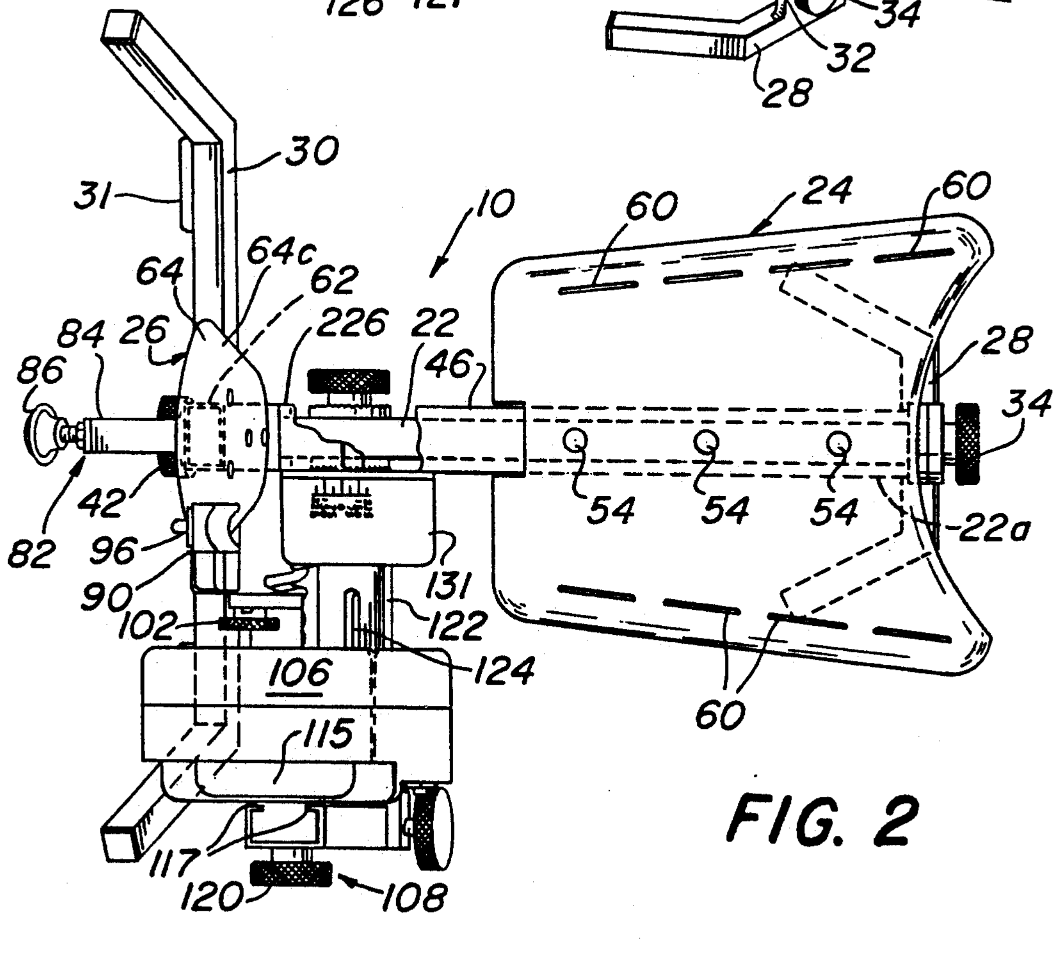
FIG. 2 is a top plan view of the device shown in FIG. 1.
Figure 4:
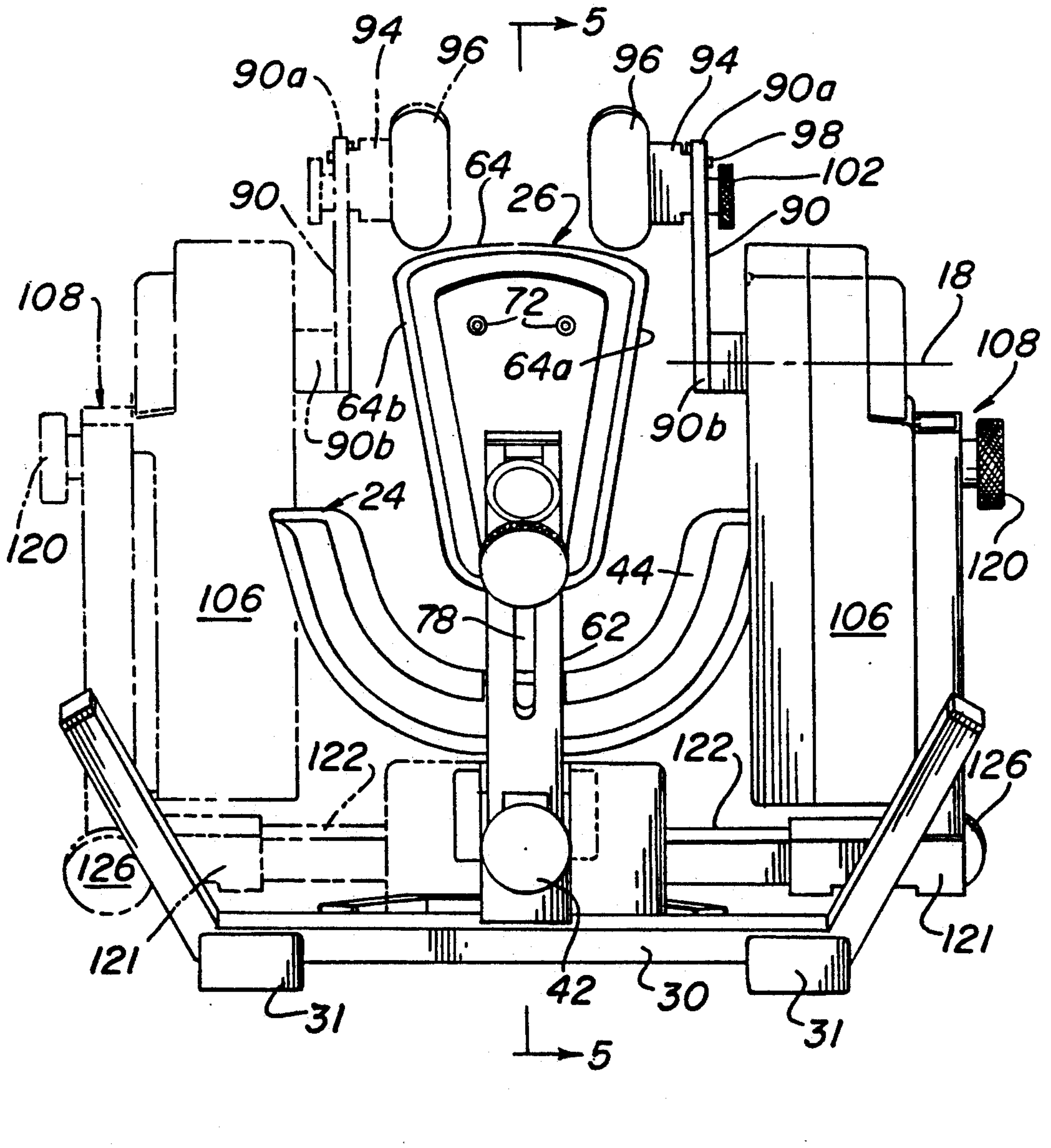
FIG. 4 is a left side elevational view of the device shown in FIG. 1.
Figure 5:
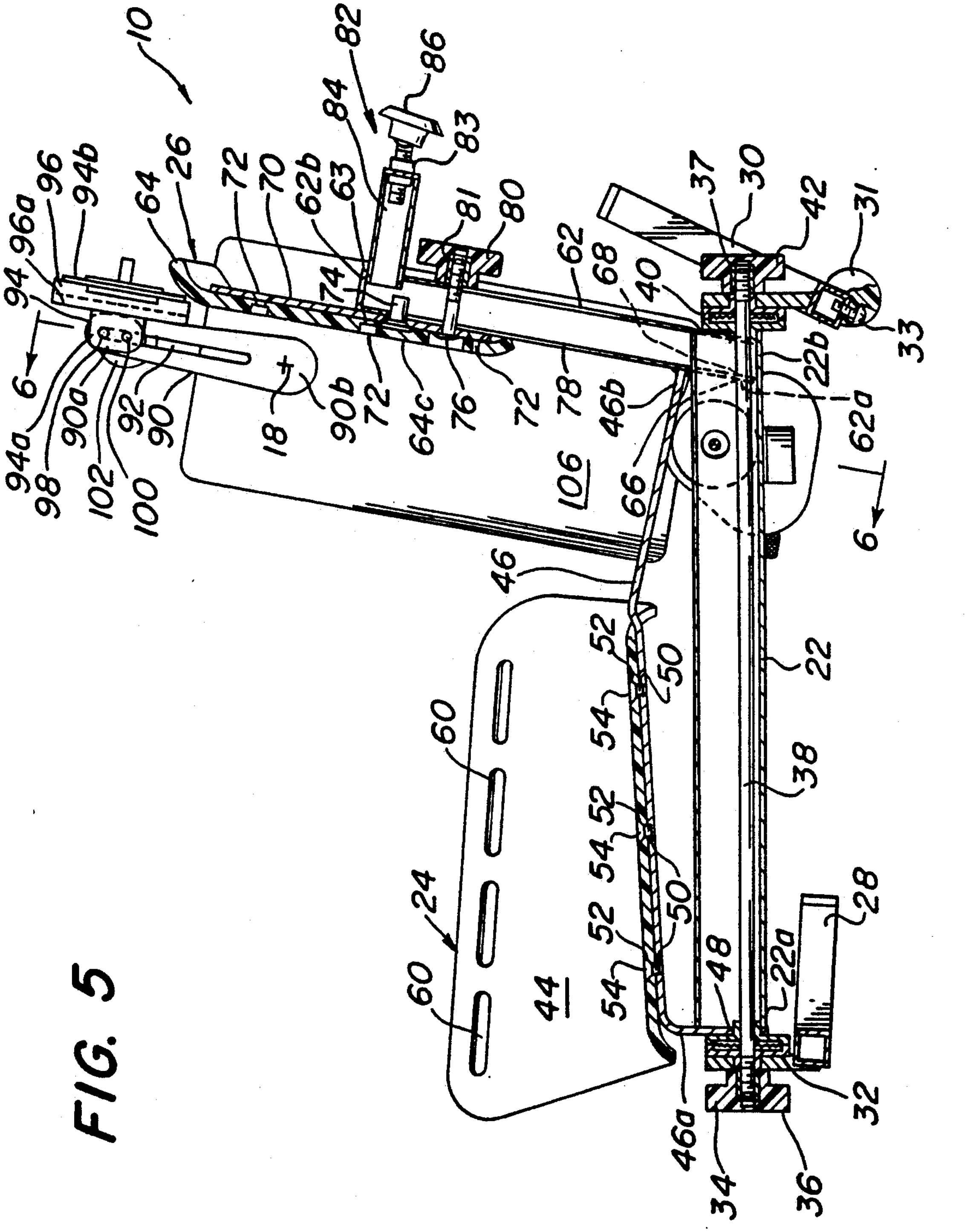
FIG. 5 is a cross-sectional view of the device shown in FIG. 4 taken along line 5—5 of FIG. 4.

Referring now to FIGS. 2, 4 and 5, the CPM 10 includes mounting means for securely receiving the foot 14. In the present embodiment, it is preferred that the mounting means be comprised of a base 22 having a proximal end 22*a* and a distal end 22*b*. A first mounting member 24 is secured to the base 22 for receiving the calf 16 and a second mounting member 26 is secured to the distal end 22*b* of the base 22 for receiving the foot 14, as described in more detail hereinafter.

In the present embodiment, it is preferred that the base 22 be comprised of an elongate hollow tube which is generally rectangular in cross section. However, it is understood by those skilled in the art that the base 22 could be configured in other manners. For instance, the base 22 could be solid and generally circular in cross section without departing from the spirit and scope of the invention.

Figure 3:
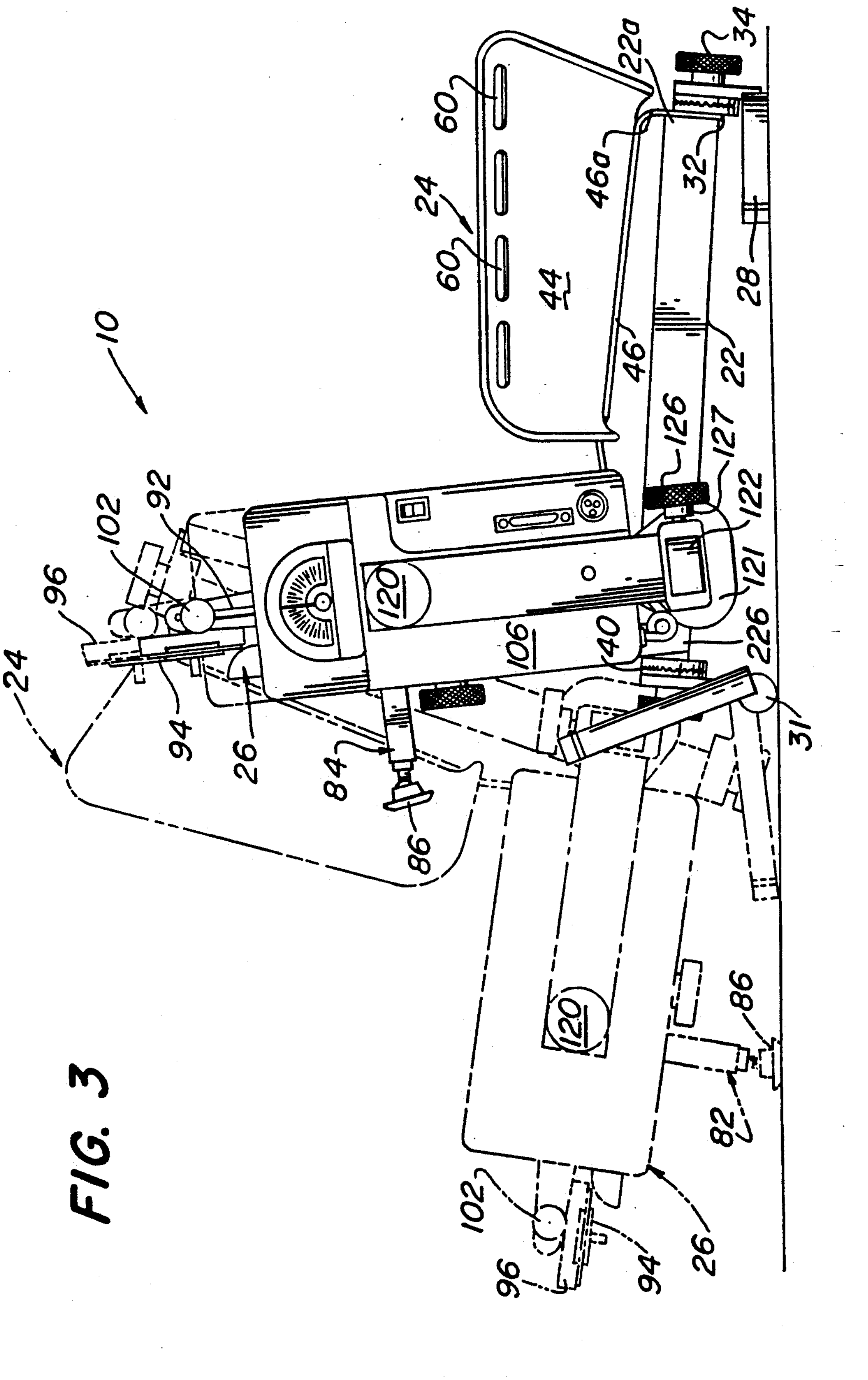
FIG. 3 is a front elevational view of the device shown in FIG. 1.

Referring now to FIGS. 1, 3 and 5, the base 22 includes a first support leg 28 extending from the proximal end 22*a* thereof and a second support leg 30 extending from the distal end 22*b* thereof. The first support leg 28 is generally U-shaped in plan view (see FIG. 2) and is adjustably secured to the proximal end 22*a* of the base 22. That is, a standard matching saw tooth or detent connection 32 is disposed between the first support leg 28 and the proximal end 22*a* of the base 22 for allowing the first support leg 28 to be positioned at a variety of angles with respect to the longitudinal axis of the base 22. The matching saw tooth connection 32 is provided with a knurled knob 34 having a threaded bore 36 for receiving a threaded shaft 38 disposed within the base 22 and matching saw tooth connection 32 for providing a mechanism for locking the matching saw tooth connection 32 at a particular angle (see FIG. 5).

Referring now to FIGS. 3-5, the second support leg 30 is also generally U-shaped in plan view and includes a pair of elastomeric pads 31 (see FIG. 4) along the lower edge thereof for preventing the second support leg 30 from marring the support surface 11 the CPM 10 is supported on. The elastomeric pads 31 are secured to the second support leg 30 by a standard fastener, such as a screw 33. A second matching saw tooth connection 40 is interposed between the second support leg 30 and the distal end 22*b* of the base 22. The second matching saw tooth connection 40 also includes a knurled knob 42 having a threaded bore 37 for receiving one end of the threaded shaft 38. The first and second support legs 28 and 30 are identically mounted on the proximal and distal ends 22*a*, 22*b* of the base 22. The matching saw tooth connections 32, 40 are well understood by those skilled in the art and, therefore, further description of the matching saw tooth connections 32, 40 is omitted for purposes of convenience only and is not limiting.

Referring now to FIGS. 1-3 and 5, in the present embodiment, it is preferred that the first mounting member 24 be comprised of a generally trough-shaped shell 44 secured to the base 22 by a mounting bracket 46. The mounting bracket 46 is positioned above the base 2 and is secured to the base 22 at the proximal and distal ends 22*a*, 22*b* thereof. That is, the mounting bracket 46 has a proximal end 46*a* having an aperture 48 which receives the threaded shaft 38 and a portion of the first matching teeth connection 32 to thereby secure the proximal end 46*a* of the mounting bracket 46 to the proximal end 22*a* of the base 22. The mounting bracket 46 also includes a distal end 46*b* which is secured to the second mounting member 26 proximate the distal end 22*b* of the base 22 by a standard fastening method, such as welding, as described in more detail hereinafter.

As best shown in FIG. 5, the mounting bracket 46 includes three threaded apertures 50 which correspond to three countersink apertures 52 in the shell 44. Standard fasteners, such as flathead screws 54, are disposed through the countersink apertures 52 into threaded engagement with the threaded apertures 50 of the mounting bracket 46 to thereby secure the shell 44 thereto. In the present embodiment, it is preferred that the shell 44 be constructed of a polymeric material, such as polyvinyl chloride. However, it is understood by those skilled in the art that the shell 44 could be constructed of other materials, such as aluminum. Similarly, it is also understood by those skilled in the art that the shell 44 could be secured to the mounting bracket 46 in other manners, such as by rivets or welding if the shell were constructed of a metallic material.

As best shown in FIGS. 1, 2 and 5, the first mounting member 24 includes securing means for securing the calf 16 to the first mounting member 24. In the present embodiment, it is preferred that the securing means be comprised of standard soft goods 58 which interlock with the shell 44 to retain the calf 16 thereon. That is, the soft goods 58 are comprised of a series of soft straps 58*a* which extend through a series of elongate slots 60 at the upper end of the shell 44. It is understood by those skilled in the art that the soft goods 58 do not form a part of the present invention and, therefore, further description thereof has been omitted for purposes of convenience only and is not limiting.

Referring now to FIGS. 2, 4 and 5, in the present embodiment, it is preferred that the second mounting member 26 be comprised of a hollow tube 62 which is generally rectangular in cross section and extends upwardly from the distal end 22*b* of the base 22. The second mounting member 26 further includes a generally flat plate 64 for receiving the foot 14. The plate 64 is preferably slideably disposed on the tube 62. A first end 62*a* of the tube 62 is positioned within an aperture 66 in the distal end 22*b* of the base 22. The first end 62*a* of the tube 62 includes a mounting aperture 68 for receiving the threaded shaft 38 therethrough to thereby assist in securing the tube 62 to the base 22. The second end 46*b* of the mounting bracket 46 is secured to the first end 62*a* of the tube 62 proximate the distal end 22*b* of the base 22 by welding the same together. Similarly, the first end 62*a* of the tube 62 is welded to the distal end 22*b* of the base 22.

The plate 64 is preferably constructed of a polymeric material, such as polyvinyl chloride. However, it is understood by those skilled in the art that the plate 64 could be constructed of other materials, such as wood or a metallic material. The plate 64 includes a mounting bracket 70 which is secured to the plate 64 by a plurality of standard fasteners, such as screws 72. The mounting bracket 70 includes a pin 74 and a bolt 76 which extend into an elongate slot 78 in the tube 62. A knurled knob 80 having a threaded bore 81 threadably receives the bolt 78 on the opposite side of the tube 62 for allowing the plate 64 to be adjustably positioned at any point along the length of the tube 62. The pin 74 serves to prevent the plate 64 from pivoting with respect to the tube 62.

Referring now to FIGS. 3 and 5, the second mounting member 26 includes a third support leg 82 extending therefrom. The third support leg 82 is comprised of a generally cylindrical tube 84 which extends transversely from the upper or second end 62*b* of the tube 62 in the distal direction. That is, the support leg tube 84 is positioned within a complementary aperture 63 at the upper end 62*b* of the tube 62 and is secured thereto by a standard fastening method, such as welding. A pad 86 for engaging the support surface 11 is threadably secured to the end of the cylindrical tube 84 by a nut and bolt mechanism 83 for allowing the length of the third support leg 82 to be adjusted, as is understood by those skilled in the art.

As best shown in FIG. 3, the first, second and third support legs 28, 30 and 82 permit the CPM 10 to be positioned in a first operative configuration (shown in solid lines) wherein the first and second support legs 28, 30 support the CPM 10 and a second operative position (shown in phantom) wherein the second and third support legs 30, 82 support the CPM 10. In the first operative configuration, the patient uses the CPM 10 with the calf 16 generally parallel to the support surface 11 of the CPM 10. In the second operative configuration, the patient's foot 14 is positioned generally parallel to the support surface 11 of the CPM 10. Thus, the CPM 10 of the present invention is versatile in that it allows the patient to assume one of two positions while the toe 12 is being exercised, as described in more detail hereinafter.

As shown in FIG. 1, the second mounting member 26 includes securing means for securing the foot 14 to the plate 64. In the present embodiment, it is preferred that the securing means be comprised of a strap 88 having hook and loop material (not shown) thereon for being positioned about the foot 14 and plate 64 to thereby secure the foot 14 to the plate 64. While in the present embodiment, it is preferred that the securing means be comprised of a strap 88, it is understood by those skilled in the art that other means could be utilized to secure the foot 14 to the second mounting member 26. For instance, the plate 64 could be configured as an opened toed shoe (not shown) for securely receiving the foot 14.

While in the present embodiment, it is preferred that the mounting means be comprised of the base 22, first mounting member 24 and second mounting member 26, it is understood by those skilled in the art that the present invention is not limited to any particular means for securely holding the calf 16 and foot 14 in place. For instance, the first and second mounting members 24, 26 could be omitted and replaced with a boot-type structure without departing from the spirit and scope of the invention.

Referring now to FIGS. 1 and 4–6, the CPM 10 includes a carriage member 90 positioned proximate the mounting means having a first end 90*a* for receiving the toe 12 and a second end 90*b*. More particularly, the carriage member 90 is positioned proximate the second mounting member 26. That is, as shown in FIG. 4, the plate 64 of the second mounting member 26 includes a first side 64*a* and a second side 64*b*. The carriage member 90 can be selectively positioned proximate either the first or second side 64*a*, 64*b* of the plate 64 such that the CPM 10 is bilateral, as described in more detail hereinafter.

Figure 6:
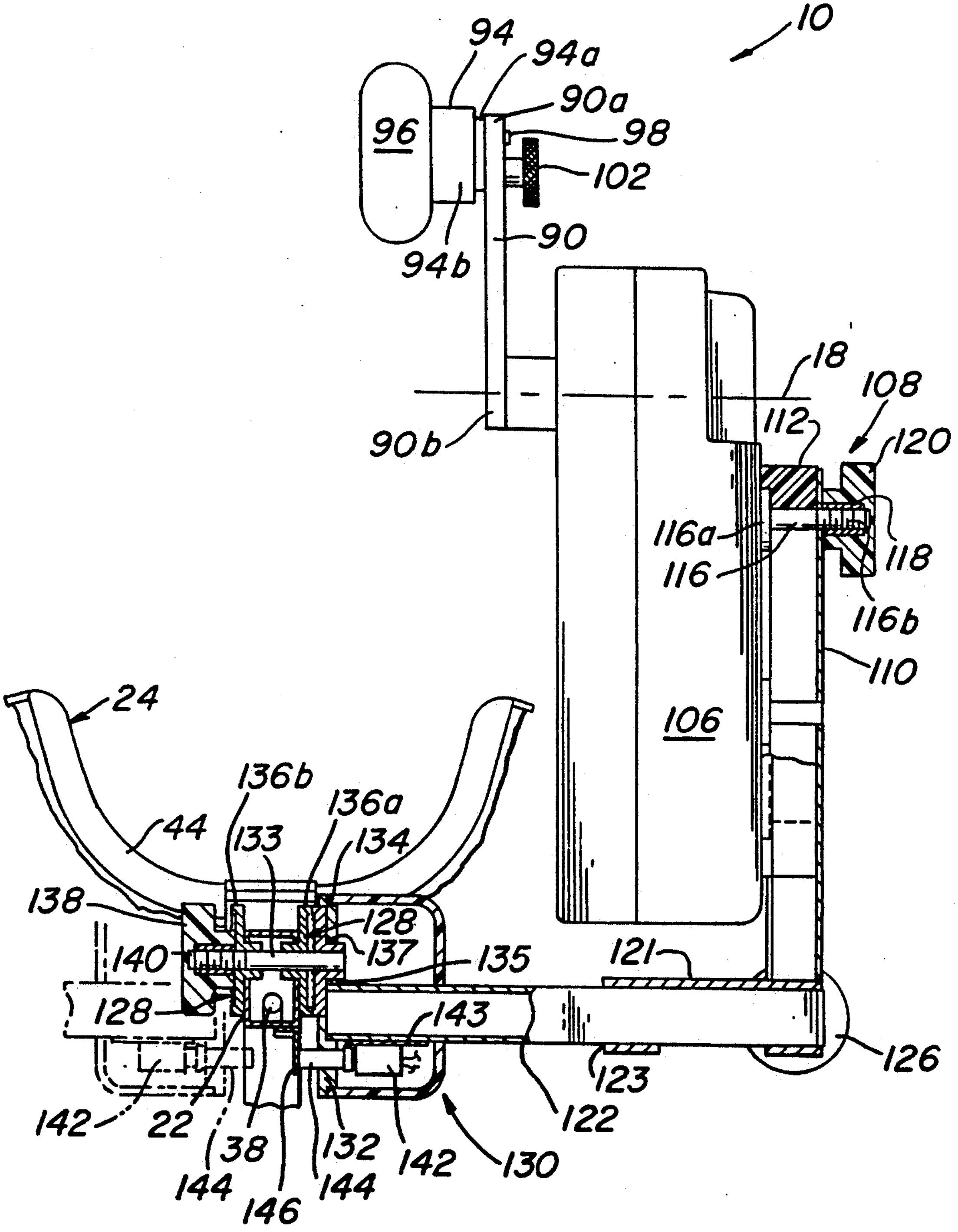
FIG. 6 is a cross-sectional view of the device shown in FIG. 5 taken along line 6—6 of FIG. 5.

Referring now to FIGS. 5 and 6, the carriage member 90 includes an elongate slot 92 therein. Slideably mounted on the carriage member 90 is an L-shaped member 94. A first leg 94*a* of the L-shaped member 94 is in facing engagement with the first carriage member 90 and extends generally transversely with respect to the plate 64. A second leg 94*b* extends generally transversely from the first leg 94*a* and extends toward the plate 64. The second leg 94*b* includes a pad 96 mounted thereon which includes a surface 96*a* for receiving the toe 12. Extending outwardly from the first leg 94*a* is a pin 98 and a threaded bolt 100. The threaded bolt 100 and pin 98 extend through the slot 92 such that the L-shaped member 94 is slideably disposed on the carriage member 90. A knurled knob 102 includes a threaded bore (not shown) for receiving the threaded bolt 100 to thereby fix the L-shaped member 94 at any position along the length of the slot 92, as is well understood by those skilled in the art.

As shown in FIG. 1, the carriage member 90 includes securing means for securing the toe 12 to the surface 96*a* of the pad 96. In the present embodiment, it is preferred that the securing means be comprised of a standard strap 104 having hook and loop material thereon (not shown) for securely retaining the toe 12 on the pad 96. However, it is understood by those skilled in the art that other means could be utilized to secure the toe 12 to the pad 96. For instance, the pad 96 could be configured in the form of a cup (not shown) to receive the toe 12.

Referring now to FIGS. 4–8, the CPM 10 includes a drive means interconnected between the second end 90*b* of the carriage member 90 and the mounting means for oscillating the first end 90*a* of the carriage member 90 about the second end 90*b* thereof with respect to the mounting means to thereby move the toe 12 between dorsiflexion and plantar flexion. More particularly, the drive means is interconnected between the second end 90*b* of the carriage member 90 and the base 22 for oscillating the first end 90*a* of the carriage member 90 about the second end 90*b* thereof with respect to the second mounting member 26 or plate 64.

As mentioned previously, the carriage member 90 includes a pad 96 having a surface 96*a* for receiving the toe 12. Similarly, the plate 64 of the second mounting member 26 includes a surface 64*c* for receiving the foot 14. Referring now to FIG. 5, the drive means has a neutral position wherein the surface 64*c* of the plate 64 and surface 96*a* of the pad 96 are generally planar (not shown), an extension position wherein the surface 96*a* of the pad 96 is positioned to the left of the surface 64*c* of the plate 64 and a flexion position wherein the surface 96*a* of the pad 96 is positioned to the right (not shown) of the surface 64*c* of the plate 64. The drive means moves the surface 96*a* of the carriage member 90 between the neutral, extension and flexion positions to thereby obtain continuous passive motion.

The drive means moves the carriage member 90 a maximum of approximately ninety degrees (90°) from the neutral position in the extension direction and approximately sixty degrees (60°) from the neutral position in the flexion direction. However, it is understood by those skilled in the art that the range of motion of the carriage member 90 can be selected in accordance with the desires of the patient or therapist, as described in more detail hereinafter.

Referring now to FIGS. 1 and 6, in the present embodiment, it is preferred that the drive means be positioned within a housing 106 interconnected between the carriage member 90 and base 22. As described in more detail hereinafter, the housing 106 includes the control circuitry and drive elements for moving the carriage member 90 with respect to the plate 64. In the present embodiment, the carriage member 90 is pivotally mounted on the housing 106 such that the first end 90*a* of the carriage member 90 pivots about the second end 90*b* thereof. That is, the drive means rotates the second end 90*b* of the carriage member 90 to thereby pivot the first end 90*a* thereof, as described in more detail hereinafter.

Referring now to FIGS. 1, 2 and 6, since the CPM 10 is used with patients of varying size, it is necessary that the housing 106 be adjustably mounted on the base 22 to permit the pad 96 to readily receive the toe 12. To this end, the housing 106 can be adjusted vertically with respect to the base 22 by a telescopically expanding adjustment mechanism 108. The adjustment mechanism 108 is comprised of an outer generally U-shaped channel 110 which slideably receives a complementary inner block 112. The outer channel 110 and inner block 112 are generally rectangular in cross section. The block 112 is secured to the housing 106 by a standard fastener 113 and includes a pair of grooves 115 which slideably receive a pair of flanges 117 on the outer channel 110 (as shown in FIG. 2). The inner block 112 includes an elongate slot 114. A bolt 116 having a head 116*a* slideably positioned between the inner block 112 and housing 106 includes a threaded shaft 116*b* which extends through the slot 114. The threaded shaft 116*b* is threadably positioned within a threaded bore 118 of a knurled knob 120. By tightening and loosening the knob 120, a clamping force is applied between the inner block 112 and outer channel 110 to secure the same together or permit the same to move with respect to each other and thereby adjust the vertical height of the housing 106.

Referring now to FIGS. 1 and 6, since human feet are of varying width, it is necessary to adjust the position of the first end 90*a* of the carriage member 90 towards and away from the respective side 64*a*, 64*b* of the plate 64 to accommodate the width of the foot to be exercised. To accomplish this, the lower end 110*b* of the outer channel 110 includes a block 121 for slideably receiving a cantilevered member 122 through a complementary opening 123 therein. The cantilevered member 122 includes an elongate slot 124 which receives at least one pin (not shown) extending from the block 121 to allow the outer channel 110 to slide with respect to the cantilevered member 122. A knurled knob 126 includes a threaded bolt 127 (see FIG. 3) extending therefrom and through a complementary threaded hole (not shown) in the block 121 into engagement with the cantilevered member 122 to thereby provide a set screw-type mechanism, as is well understood by those skilled in the art. Thus, the block 121, outer channel 110, housing 106 and carriage member 90 are selectively slideably disposed on the cantilevered member 122 to thereby adjust the distance between the first end 90*a* of the carriage member 90 and the plate 64 to accommodate different width feet.

Referring now to FIGS. 4 and 6, the CPM 10 is bilateral because the housing 106 and carriage member 90 are positionable on either the first side 64*a* of the plate 64 or the second side 64*b* of the plate 64 (as shown in phantom in FIG. 4). This bilateral function is accomplished by a pair of matching saw tooth connections 128 disposed at the distal end 22*b* of the base 22. As best shown in FIG. 6, the cantilevered member 122 includes a housing 130 proximate the end thereof closest to the base 22. The housing 130 includes a base plate 132 having a bore 135 for securely receiving the cantilevered member 122. That is, the cantilevered member 122 is secured within the bore 135 by a standard fastening method, such as welding.

The base plate 132 includes a housing coupling element 134 which forms part of the matching saw tooth connection 128. The housing coupling element 134 is welded within an aperture 137 in the base plate 132. A bolt 133 extends from the center of the housing coupling element 134 and has a length sufficient to extend through or across the base 22. Secured to opposite sides of the base 22 are a pair of complementary base coupling elements 136*a*, 136*b* which include teeth that match the teeth on the housing coupling element 134. Extending through the center of the base coupling elements 136 is a bore for receiving the bolt 133. A knurled knob 138 having a threaded bore 140 receives the bolt 133 to thereby securely retain the housing coupling element 134 in engagement with the base coupling element 136*a* on the right side of the base 22, as shown in FIG. 6. That is, the housing coupling element 134 can be positioned in engagement with the base coupling element 136*a*, 136*b* on either side of the base 22 to thereby mount the housing 106 and carriage member 90 on either side of the plate 64.

Referring now to FIG. 6, the drive means within the housing 106 is controlled by a microprocessor 170 which is suitably programmed, as described in more detail hereinafter. The programming includes parameters which relate to whether the housing 106 is positioned on the first or second 64*a*, 64*b* side of the plate 64. A microswitch 142 is in electrical communication with the microprocessor via wires 143 to provide a signal indicating whether the housing 106 is on the first or second side 64*a*, 64*b* of the plate 64. The switch 142 includes an actuator 144 which extends through an aperture in the base plate 132 beneath the base 22. One lateral side of the base 22 includes a plate 146 extending downwardly therefrom.

When the housing 130 is secured to the side of the base 22 with the plate 146, the actuator 144 is depressed to thereby close the switch 142 and send a signal to the microprocessor that the housing 106 is located on the side of the base 22 for the right foot. Similarly, when the housing 130 is positioned on the opposite side of the base 22 (as shown in phantom in FIGS. 4 and 6), the actuator 144 is not depressed thereby opening the switch 142 and sending a second type of signal to the microprocessor indicating that the housing 106 and carriage member 90 are on the side of the base 22 for the left foot. It is necessary that the microprocessor determine whether the housing 130 is positioned on the right or left side of the base 22 in order to properly control the direction of actuation of the carriage member 90. That is, movement of the carriage member 90 in the dorsiflexion or plantar flexion direction depends upon which side of the base 22 the housing 130 is mounted.

As shown in FIGS. 2 and 6, a portion of the cantilevered member 122 and housing coupling element 134, as well as the switch 142, are positioned within a cover 131 which provides the housing 130 with an aesthetic quality. A series of angular graduations 139 are marked on the cover 131 to indicate the angle at which the housing 106 extends from the base 22. In the present embodiment, it is preferred that the cover 131 be constructed of a polymeric material, such as polyvinyl chloride. However, it is understood by those skilled in the art that the cover 131 could be constructed of other materials, such as wood or a metallic material, or could be entirely omitted.

Figure 7:
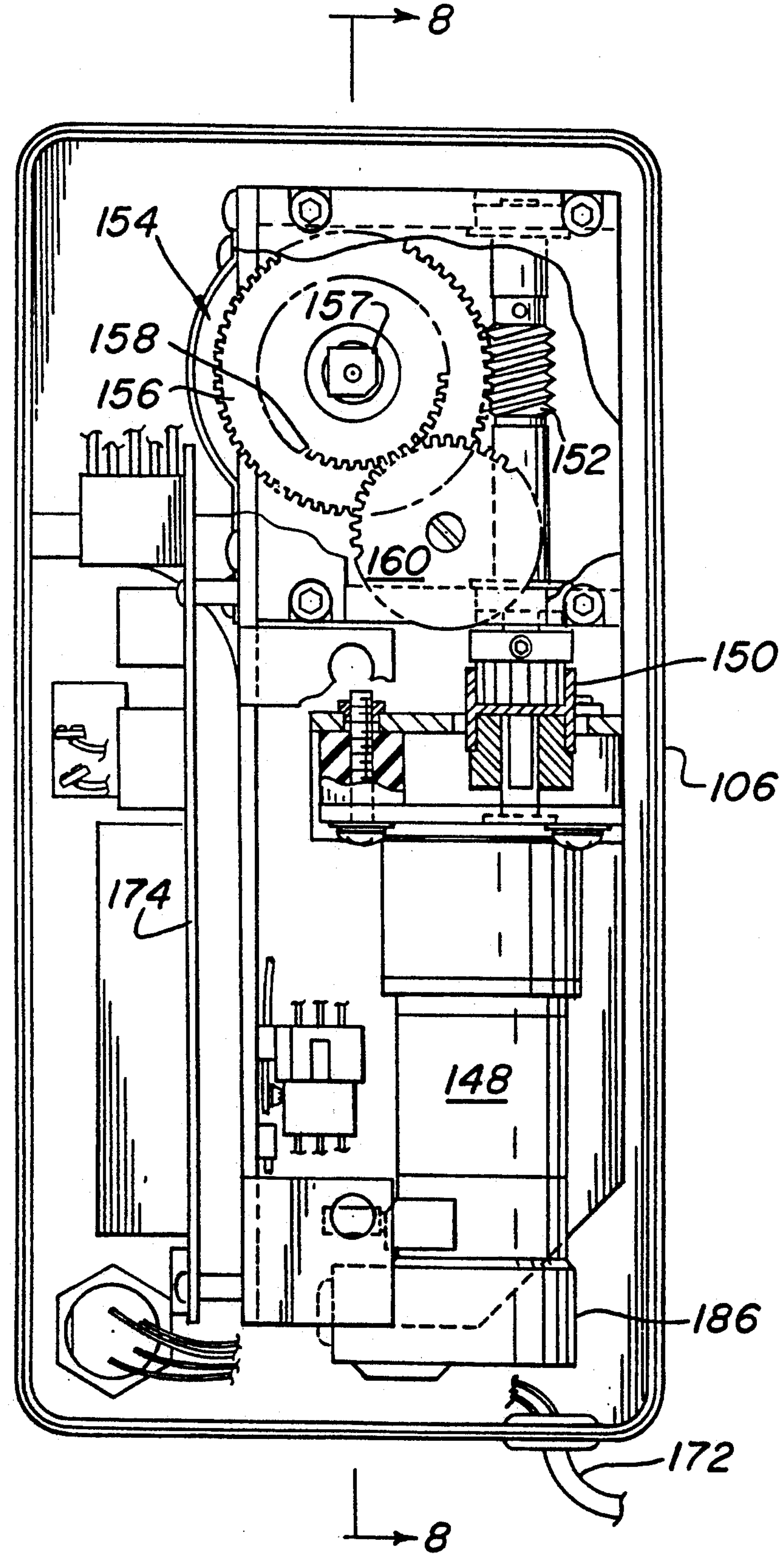
FIG. 7 is an elevational view, partially broken away and partially in cross section, of a drive mechanism for the device shown in FIG. 1.
Figure 8:
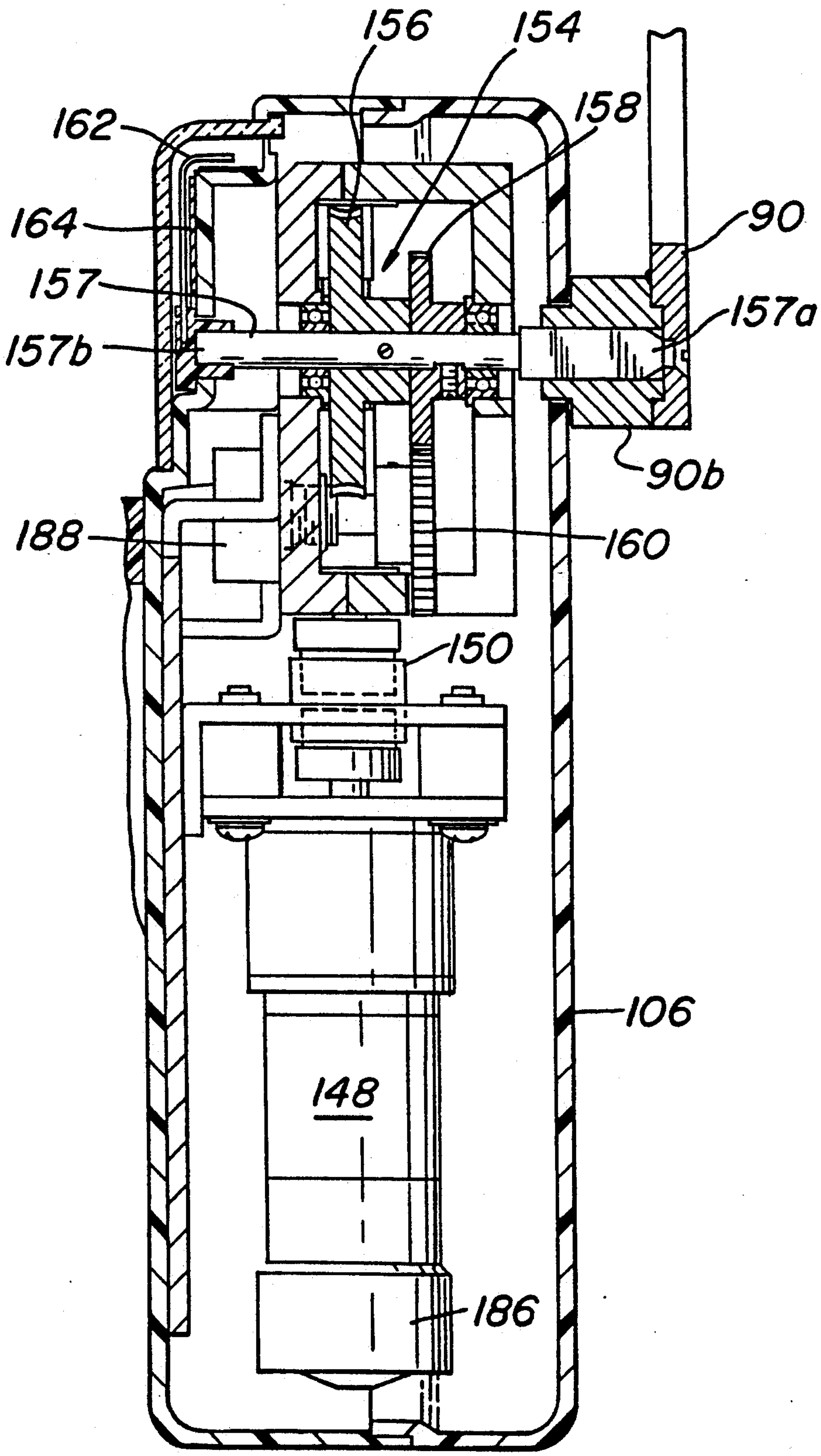
FIG. 8 is a cross-sectional view of the drive mechanism shown in FIG. 1 taken along line 8—8 of FIG. 7.

Referring now to FIGS. 7 and 8, in the present embodiment, it is preferred that the drive means be comprised of a DC motor 148 drivingly connected to a break away torque coupling element 150 which is in driving engagement with a worm gear 152. The worm gear 152 is in driving engagement with a compound gear 154. The compound gear 154 includes a large spur gear 156 which is in driving engagement with the worm gear 152 and a small spur gear 158 which is in driving engagement with a spur gear potentiometer 160. The large spur gear 156 includes a shaft 157 having a first end 157*a* which is in direct engagement with the second end 90*b* of the carriage member 90 to thereby provide a direct drive mechanism. The shaft 157 includes a second end 157*b* having a radially extending indicator needle 162 thereon which overlies a series of marked angular graduations 164 on the face of the housing 106 to indicate the angular position of the carriage member 90.

While in the present embodiment, it is preferred that the drive means be comprised of a DC motor 148, break away torque coupling 150, worm gear 152 and compound gear 154, it is understood by those skilled in the art that other means could be used to drive the second end 90*b* of the carriage member 90. For instance, a planetary gear mechanism could be incorporated between the DC motor 148 and second end 90*b* of the carriage member 90. It is also understood by those skilled in the art that this particular drive means does not form a part of the present invention and, therefore, the description thereof is necessarily brief for purposes of convenience only and is not limiting.

The drive means includes a speed control means for controlling the velocity of the carriage member 90. The speed of the carriage member 90 is directly related to the speed of the DC motor 148. If the velocity of the carriage member 90 is too fast, the number of turns per second of the motor 148 is decreased. If the velocity of the carriage member 90 is too slow, the number of turns per second of the motor 148 is increased.

In the preferred embodiment, the carriage member 90 pivots about the second end 90*b* thereof with respect to the second mounting member 26 or plate 64 at a substantially constant velocity. Since in the preferred embodiment, the drive means directly drives the carriage member 90, by maintaining a constant velocity of the drive means, a constant angular velocity of the carriage member 90 is also maintained.

Figure 9:
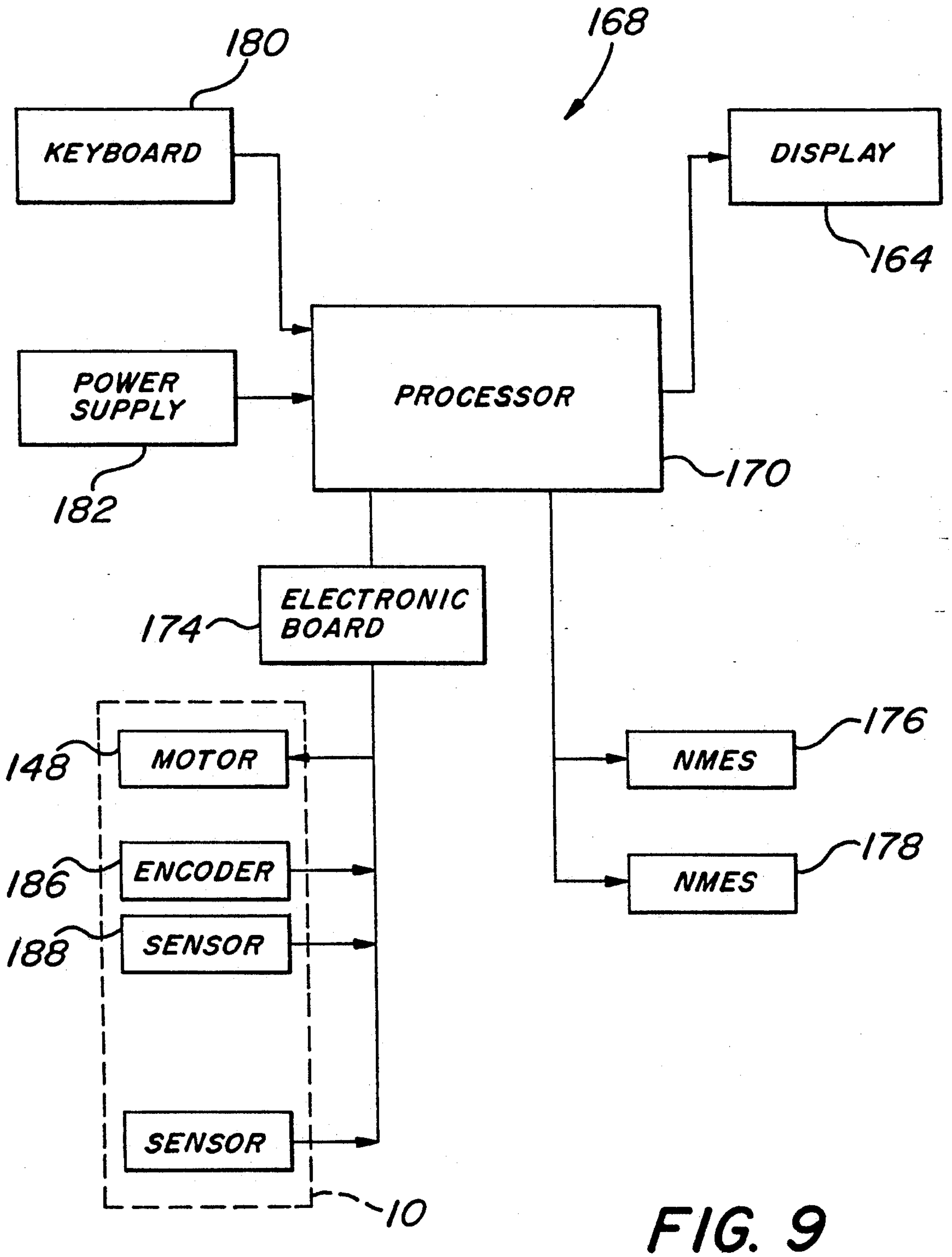
FIG. 9 is a general block diagram of a control system for the device shown in FIG. 1 in accordance with the present invention.

As shown in FIGS. 7 and 9, the speed control means includes a velocity sensor 186 for determining the velocity of the carriage member 90. In the preferred embodiment, the velocity sensor is an optical encoder 186 (not shown) located on the armature (not shown) of the motor 148 which determines the number of turns of the motor per second.

The control unit 168 receives signals from the optical encoder 186 associated with the motor 148 which corresponds to the actual speed of the motor 148. The optical encoder 186 provides an on/off type pulse train for motor speed feedback. Because the carriage member 90 is directly driven, the motor pulse rate is directly proportional to the angular rate. Therefore, the CPM 10 maintains constant angular speed by maintaining a constant motor pulse period.

The encoder 186 sends a pulse signal to an electronic board 174 which transmits the signals to the control unit 168. The electronic board 174 comprises two integrated circuits (not shown). The first integrated circuit comprises a voltage regulator which is connected to a five volt power input pin located on the control unit. The second integrated circuit contains an H-bridged motor driver chip which acts as a switch and is connected to the motor leads. The motor driver chip determines the direction in which the motor 148 is rotating. The motor driver chip also acts as a on/off switch such that the motor 148 is controlled by pulse width modulation. In addition, safety switches are connected to the motor lead so that in the case of certain fault detections, the motor 148 is automatically shut off.

A second sensor 188 is positioned within the housing 106 for determining the position at which the carriage member 90 pivots about the second end 90*b* thereof with respect to the second mounting member 26. In the present embodiment, the second sensor 188 comprises the spur gear potentiometer 160 which is in driving engagement with the smaller spur gear 158 at a one-to-one ratio. Potentiometer gears are well known to those skilled in the art. Accordingly, further description thereof is omitted for purposes of convenience only and is not limiting. The spur gear potentiometer 160 is in electrical communication through a wire 172 with a control unit 168, which allows the therapist to control the operation of the CPM 10.

The control unit 168 includes a microprocessor 170 for receiving signals from the switch 1 42, spur gear potentiometer 160 and the optical encoder 186 associated with the motor 148. The microprocessor 170 includes suitable programming which correlates the signals from the spur gear potentiometer 160 and optical encoder 186 and controls the amount of power applied to the motor 148, and thus the speed of the same. Similarly, the microprocessor 170 includes suitable programming which correlates the position of the switch 142 (i.e., either on or off), and determines the parameters selected by the controller for determining the operating limits of the toe device 10.

In the preferred embodiment, the off position of the switch 142 sets the parameter for a hallux toe on one foot and the on position of the switch sets the parameters for the contralateral hallux toe on the other foot. It is understood by those skilled in the art that the designation of on position or off position for the right toe or the left toe is arbitrary and does not affect the scope and spirit of the present invention. In the present embodiment, it is preferred that the control unit 168 include an input device for inputting information into the microprocessor 170 which corresponds to the therapist's desired operation of the CPM. In the preferred embodiment, it is preferred that the input device be a keyboard 180 or keypad, as is understood by those skilled in the art.

The microprocessor 170 is powered by a standard power supply 182. To confirm that the desired operating characteristics are input correctly and to display operational data (e.g., speed, range of motion, etc.), the control unit 168 is provided with a display 184, such as a liquid crystal display. It is understood by those skilled in the art that other displays could be used, such as a cathode ray tube or a printer (not shown).

The microprocessor 170 is programmed to provide comparing means for comparing the actual or determined velocity with a predetermined velocity inputted into the control unit 168 by the therapist or to a default predetermined velocity if a desired velocity is not inputted into the control unit as stored within the microprocessor 170. In the preferred embodiment, the equation for ascertaining the speed constant is as follows:

$$\text{speed constant} = \frac{(60 \text{ sec./min.} * 24°\text{/rev})}{(286 * 16 \text{ pulse/rev.} * 85.33 \text{ usec}}$$

wherein

24°/rev=motor shaft speed

286=gear ratio 16 pulse/rev.=optical encoder speed 85.33 usec=time constant

The velocity is preferably in the range of 4° per minute to 180° per minute. The determined velocity is ascertained by the microprocessor 170 which analyzes the signals from the optical encoder 186 over time, as is understood by those skilled in the art. The microprocessor 170 adjusts the velocity of the carriage member 90 as it pivots about the second end **90*b* thereof with respect to the second mounting member 26 if the determined velocity is different than the predetermined velocity by a preset limit, as is determined by tables stored within the microprocessor 170. The velocity of the carriage member 90** is adjusted such that the determined velocity is substantially equal to the predetermined velocity.

More particularly, the velocity of the carriage member 90 is controlled by pulse width modulation of the power supply to the motor 148 in response to motor speed feedback from the optical encoder 186. The power ON pulse width is set by the encoder pulse indicating that the motor 148 is in motion. The OFF pulse width is set by a transfer function that uses encoder count during previous off periods, and the desired velocity. The control of the ON pulse insures that sufficient power is applied to overcome inertia, friction and motor reflective load. During the off period, the encoder count provides an indication of motor coast which compensates for varying loads. The desired speed as determined by the user sets the nominal off period.

As mentioned above, in the preferred embodiment the carriage member 90 can be set to have a maximum range of motion from −60° to +90° with respect to a vertical axis. As the carriage member 90 completes a motion in a particular direction, the carriage member 90 pauses for a preset time so that a pair of controlled, external stimulators (NMES) 176, 178 may be applied to the muscles. An NMES is an electronic device that attaches to the muscles of the toe 12 to stimulate muscle contraction or relaxation. A first NMES 176 is provided for stimulating a muscle of the toe 12 is at a pause period implemented when the toe 12 at the maximum dorsiflexion position and a second NMES 178 is provided for stimulating a muscle of the toe 12 during a pause period implemented when the toe 12 is at the maximum plantar flexion position. The therapist decides which muscles to stimulate into contraction or relaxation. Of course, the therapist could opt to omit the use of the NMES' 176, 178 entirely. NMES' are well known to those skilled in the art and, therefore, further description thereof is omitted for purposes of convenience only and is not limited.

The CPM 10 can sense stroke completion of the carriage member 90 by measuring the angle formed between the carriage member 90 and a vertical axis (not shown) using the potentiometer 160 and comparing the same to the range of motion input into the control unit 168 by the operator or to a default value. Other means can be used to sense stroke completion of the carriage member 90, such as an encoder (not shown) mounted on the second end **90*b* of the carriage member 90 which can sense when the second end 90*b*** stops and reverses direction.

It is understood by those skilled in the art that other methods or devices can be used to control the CPM 10. For instance, the controller described in the U.S. patent application Ser. No. 07/760,424 entitled "Universal Controller for Continuous Passive Motion Devices", filed Sep. 16, 1991, can be used to control the operation of the CPM 10. Accordingly, U.S. patent application Ser. No. 07/760,424 is hereby incorporated by reference in its entirety.

In use, the patient is positioned proximate the CPM 10 and the various adjustment mechanisms described above are adjusted to the desires of the patient or therapist to place the toe 12 in engagement with the pad 96 on the first end **90*a* of the carriage member 90. The straps 58, 88 are then used to secure the calf 16 and foot 12 of the patient to the shell 44 and plate 64, respectively. The therapist then actuates the control unit 168 and inputs the desired operating information, including velocity, range of motion, force, duration, etc. After the desired operating information is input into the control unit 168 through the keyboard 180, the therapist instructs the CPM 10** to begin operation.

Assuming the first end **90*a* of the carriage member 90 is positioned in alignment with the plate 64, the carriage member 90 begins to rotate about the second end 90*b* thereof toward the plantar flexion position upon power being supplied to the motor 148. As the motor 148 rotates, it causes the shaft 157 to rotate therewith. The shaft 157 includes a first end 157*a* which is in direct engagement with the second end 90*b* of the carriage member 90 and causes the first end 90*a* of the carriage member 90 to rotate about the second end 90*b*** thereof.

As the carriage member 90 rotates toward the plantar flexion position, the microprocessor 170 monitors the relative speed of the motor 148 using the optical encoder 186. In accordance with the programming of the microprocessor 170, the microprocessor 170 provides pulse width modulation of the power supplied to the motor 148 to thereby control the speed of the motor 148 to achieve constant velocity of the carriage member 90 as it rotates about the second end **90*b* thereof. Because the CPM 10 is a direct drive device, by maintaining constant velocity of the motor 148, constant angular velocity of the carriage member 90 is maintained as it rotates about the second end 90*b*** thereof.

When the first end **90*a* of the carriage member 90 reaches the plantar flexion position, as sensed by the potentiometer 160 indicating angular position of the carriage member 90 with respect to the plate 64 and the housing 106, the microprocessor 170 then actuates the first NMES control 176 to stimulate the toe 12 depending upon how the therapist set the system prior to actuation. Once stimulation is complete, the rotational direction of the motor 148 is reversed by changing the polarity of the power such that the first end 90*a* of the carriage member 90 begins to move to the dorsiflexion position at a speed to maintain the velocity of the carriage member 90 constant. Once the first end 90***a* of the carriage member 90 reaches the dorsiflexion position, the second NMES control 178 is actuated to stimulate the toe 12. The CPM 10 then continues in the same cycle until the desired duration of operation is complete.

From the foregoing description, it can be seen that the present invention comprises a continuous passive motion orthosis device 10 for a toe 12 of a foot 14. It will be appreciated by those skilled in the art that changes could be made to the embodiment described in the foregoing description without departing from the broad inventive concept thereof. It is understood, therefore, that this invention is not limited to the particular embodiment disclosed, but is intended to cover all modifications which are within the spirit and scope of the invention, as defined by the appended claims.

We claim:

1. A continuous passive motion orthosis device for a toe of a foot, said device comprising:

mounting means including a surface for receiving the foot;

a carriage member positioned proximate the mounting means having a first end for receiving a toe and a second end, the first end of the carriage member including a surface for receiving the toe; and drive means for oscillating said first end of said carriage member about said second end thereof with respect to said mounting means to thereby move the toe between a neutral position wherein said surfaces are generally parallel, an extension position wherein said surface of said carriage member is positioned on one side of said surface of said mounting means and a flexion position wherein said surface of said carriage member is positioned on another side of said surface of said mounting means.

2. A continuous passive motion orthosis device for a toe of a foot, the foot having a first end connected to the toe and a second end connected to a calf, the first end of the foot being pivotably connected to the toe to form a joint such that the toe is pivotable with respect to the foot about a joint pivot axis, said device comprising:

a base having a proximal end and a distal end;

a first mounting member secured to said base for receiving the calf;

a second mounting member secured to said distal end of said base for receiving the foot;

a carriage member positioned proximate said second mounting member having a first end for receiving the toe and a second end;

drive means for oscillating said first end of said carriage member about said second end thereof with respect to said second mounting member to thereby move the toe between dorsiflexion and plantar flexion.

3. A continuous passive motion orthosis device as recited in claim 2 further including securing means for securing the toe, foot and calf to said carriage member, said second mounting member and said first mounting member, respectively.

4. The continuous passive motion orthosis device as recited in claim 2 wherein said second mounting member includes a first side and a second side, said carriage member being selectively positionable proximate said first and second sides of said second mounting member such that the device is bilateral.

5. The continuous passive motion device a recited in claim 2 further including a first support leg extending from said proximal end of said base, a second support leg extending from said distal end of said base and a third support leg extending from said second mounting member, the device being positionable in a first operative configuration wherein said first and second support legs support the device and a second operative position wherein said second and third support legs support the device.

6. The device as recited in claim 2 wherein said drive means further includes speed control means for controlling the velocity of said carriage member such that said carriage member pivots about said second end thereof with respect to said second mounting member at a substantially constant velocity.

7. The device as recited in claim 6 wherein said speed control means comprises:

velocity sensing means for determining the velocity of said first carriage member;

comparing means for comparing said determined velocity with a predetermined velocity;

velocity adjustment means for adjusting the velocity of said carriage member if said determined velocity is different than said predetermined velocity by a preset limit, said velocity adjustment means adjusting the velocity of said carriage member such that said determined velocity is substantially equal to said predetermined velocity.

8. The continuous passive motion orthosis device as recited in claim 1 including means for automatically adjusting the operation of the device in response to a position of the carriage member.

9. The continuous passive motion orthosis device as recited in claim 2 wherein said second mounting member and said first end of said carriage member each include a surface for receiving the foot and toe, respectively, said drive means having a neutral position wherein said surfaces are generally parallel, an extension position wherein said surface of said carriage member is positioned on one side of said surface of said second mounting member and a flexion position wherein said surface of said carriage member is positioned on another side of said surface of said mounting member.

10. The continuous passive motion orthosis device as recited in claim 9 wherein said drive means moves said surface of said carriage member between said neutral, extension and flexion positions.

* * * * *